United States Patent [19]

Englaender et al.

[11] Patent Number: 4,772,711

[45] Date of Patent: Sep. 20, 1988

[54] METHOD FOR THE PREPARATION OF 3-AMINOACRYLIC ACID ESTERS

[75] Inventors: Fritz Englaender, Bonn; Moustafa El-chahawi, Troisdorf; Wilhelm Vogt, Cologne, all of Fed. Rep. of Germany

[73] Assignee: Dynamit Nobel AG, Cologne, Fed. Rep. of Germany

[21] Appl. No.: 898,139

[22] Filed: Aug. 19, 1986

[30] Foreign Application Priority Data

Aug. 30, 1985 [DE] Fed. Rep. of Germany ....... 3531067

[51] Int. Cl.$^4$ .................. C07D 295/10; C07C 57/04
[52] U.S. Cl. .................................. 546/248; 560/38; 560/172
[58] Field of Search .................. 560/38, 172; 546/248

[56] References Cited

U.S. PATENT DOCUMENTS 2,987,491  6/1961  Bader et al. .................. 560/172 X
4,319,024  3/1982  Peeters et al. .................. 546/242 X

FOREIGN PATENT DOCUMENTS 869021  1/1979  Belgium .
2938872  4/1981  Fed. Rep. of Germany .
3037086  5/1982  Fed. Rep. of Germany .

OTHER PUBLICATIONS

Decombe; Ann. De Chemie, (1932), pp. 107–111.
Weygand et al., "Preparative Organic Chemistry" (1972), John Wiley & Sons [N.Y., London, Sydney, Toronto], pp. 528–529.
Chem. Ber. (1892) pp. 1040–1054, H. V. Pechmann.

Primary Examiner—Joseph Paul Brust
Attorney, Agent, or Firm—Felfe & Lynch

[57] ABSTRACT

Disclosed is a method for the preparation of 3-aminoacrylic acid esters by the addition of a beta-hydroxyacrylic acid esters to an aqueous solution of an amine salt.

11 Claims, No Drawings

METHOD FOR THE PREPARATION OF 3-AMINOACRYLIC ACID ESTERS

BACKGROUND OF THE INVENTION

The present invention is in a method for the preparation of 3-aminoacrylic acid esters.

The preparation of N,N-dimethylaminoacrylic acid ethyl esters by the reaction of sodium-3-hydroxyacrylic acid ethyl esters with dimethylamine hydrochloride in absolute ethanol (Annales de Chimie 10, 18 (1932) 108) is known. The synthesis, however, has a number of disadvantages. The reaction time is very long, amounting to 7 to 8 hours. Nevertheless a yield of only 41% is achieved. Working up the reaction mixture to separate the sodium chloride after the reaction has ended is technically very burdensome.

SUMMARY OF THE INVENTION

It has now been found that 3-aminoacrylic acid esters of the formula

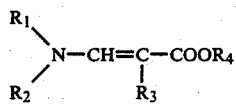

in which $R_1$ and $R_2$ represent H or identical or different straight-chain or branched alkyl moieties having 1 to 8 carbon atoms, or alkenyl moieties having 1 to 8 carbon atoms; $R_3$ represents hydrogen, straight-chain or branched alkyl moieties having 1 to 8 carbon atoms, or an isocyclic or heterocyclic or aromatic ring, or in which $R_1$ and $R_2$ in common represent a component of a 5- to 7-member ring of one or two or no double-bonds containing the amine nitrogen or additionally another nitrogen atom, and $R_4$ represents straight-chain or branched alkyl moieties having 1 to 8 carbon atoms, or an isocyclic or aromatic ring, can be obtained in excellent yields and high purities by the reaction of alkali-3-hydroxyacrylic acid esters of the formula

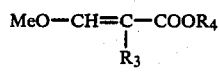

performed in an aqueous medium with salts of amines of the formula

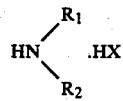

Both the amine salts and the alkali-3-hydroxyacrylic acid esters are easily soluble in water. Due to the instability of alkali-3-hydroxyacrylic acid ethyl esters in aqueous solution, it is recommended, in performing the reaction, that they be fed into an aqueous solution of the amine salt. Surprisingly, the reaction is virtually instantaneous, and the formed aminoacrylic acid ester separates itself from the water phase.

Sodium-3-hydroxyacrylic acid ester can be added to the aqueous amine salt solution as a solid compound or as a suspension in an organic solvent. Suitable organic solvents are: methyl formate, ethyl formate, methyl acetate, ethyl acetate, toluene, tetrahydrofuran, dimethoxyethane, dimethyl formamide, and acetonitrile. The preferred solvents for preparing suspensions are those which are not miscible in every ratio with water, and which may be already present in the preparation of the alkali-3-hydroxyacrylic acid ester.

The preparation of alkali-3-hydroxyacrylic acid ethyl ester preferred herein consists in the action of carbon monoxide on a suspension of sodium or potassium ethylate or methylate in ethyl acetate, so that when the reaction has ended, sodium-3-hydroxyacrylic acid ethyl ester is suspended in excess ethyl acetate. This suspension can be reacted directly with the aqueous solution of the amine salt. It is also possible to filter out the alkali salt of the 3-hydroxyacrylic acid ether ester and react it while still moist with ethyl acetate or when dry.

Yields of more than 75% with respect to the input alkali salt are achievable. Surprisingly, trimesinic acid ester is not formed. The aminoacrylic acid ester which separates from the water phase, unless organic solvents are additionally present, is of a high purity. Following a flash distillation, performed mainly to separate small amounts of inorganic substance, one obtains a distillate having an average purity of 99.5%.

The reaction of alkali-3-hydroxyacrylic acid ester with amine salts takes place at 20° to 50° C., preferably at 20° to 30° C. Lower temperatures offer no advantages. Temperatures higher than 50° C. result in lower yields.

The amine salt is advantageously used in an excess, using 1.05 to 2.5 mol of amine salt pe mol of alkali-3-hydroxyacrylic acid ester, the range from 1.1 to 1.2 mol being preferred.

The nature of the anion of the amine salt is generally not of critical importance for the reaction. Either chlorides or sulfates can be used. Moreover, the use of organic acids is also possible. Advantageously the salt is dissolved in water for the reaction. Sodium is preferred as the alkali salt in the esters of formula II, and the use of potassium is possible.

The amines of the amine salts are primary and secondary amines or ammonia. Tertiary amines do not react.

In the products and starting substances, alkyl or hydrogen are greatly preferred as $R_1$ or $R_2$. Dialkyl amines are preferred over monoalkyl amines. In dialkyl amines, $R_1$ and $R_2$ are preferably the same and have preferably 1 to 4 carbon atoms. Also preferred are piperidine and, in some cases, methylpiperidine. Alkyl moieties of 1 to 4 carbon atoms, especially methyl and ethyl, are preferred as $R_4$. Alkyl moieties having 1 to 4 carbon atoms, especially methyl and ethyl, are preferred as $R_3$, as well as benzyl and phenyl.

The amount of water in the reaction is preferably selected so that, after the reaction has ended, a 20 to 25 wt.-% sodium chloride solution will result, thus facilitating the separation of the reaction product.

The aminoacrylic acid esters are intermediates for the synthesis of heterocyclic compounds, e.g., for the synthesis of 4-hydroxyquinolines (Angew. Chem. 50 (1947); J. Am. Chem. Soc. 68 (1946) 1256).

EXAMPLE 1

138 weight-parts of solid, dried sodium-3-hydroxyethyl acrylate is added to a solution of 90 weight-parts of dimethylamine hydrochloride in 250 weight-parts of water. Soon a yellow oil separates. The oil is separated and the water phase is extracted with diethyl ether. In the subsequent vacuum distillation, 107.3 weight-parts of N,N-dimethylaminoacrylic acid ethyl ester are obtained with a purity, measured by gas chromatography, of 99.7%, corresponding to a yield of 74.8%.

EXAMPLE 2

In 340 weight-parts of ethyl acetate, 68 weight-parts of sodium ethylate are suspended, 5 weight-parts of ethyl formate are added, and the mixture is stirred at 50° C. and a carbon monoxide pressure of 50 bar. Two hours later no more carbon monoxide is being absorbed. The reaction mixture is cooled to 25° C. and poured into a solution of 90 weight-parts of dimethylamine hydrochloride in 250 weight-parts of water, so that a temperature of 30° C. is not exceeded. Stirring is continued for two more hours, and then the organic phase is separated from the aqueous phase. After distilling off the ethyl acetate, the vacuum distillation that follows yields 103.5 weight-parts of N,N-dimethylaminoacrylic acid ethyl ester with a purity of 98%, corresponding to a yield of 70.2% of the input sodium ethylate.

EXAMPLE 3

50.6 weight-parts of methylamine hydrochloride are dissolved in 100 weight-parts of water, and 69 weight-parts of dried sodium-3-hydroxyethylacrylate are added. The mixture is stirred for 2 hours and extracted with ether. After distillation, 41.0 weight-parts of methylaminoacrylic acid ethyl ester are obtained corresponding to a yield of 63.3% of the theory.

EXAMPLE 4

61.2 weight-parts of ethylamine hydrochloride are dissolved in 100 weight-parts of water, and 69 weight-parts of dried sodium-3-hydroxyethylacrylate are added. The work-up is performed as in Example 3. Yield: 54 weight-parts of ethylaminoacrylic acid ethyl ester, corresponding to a yield of 75.5% of the theory.

EXAMPLE 5

69 g of sodium-3-hydroxyethylacrylate is added to a solution of 50 weight-parts of ammonium chloride in 200 weight-parts of water and stirred for 2 hours. The mixture is extracted with ether and the ether distilled out in vacuo. 51 g is obtained of a residue containing 21% of aminoacrylic acid ethyl ester.

EXAMPLE 6

175 weight-parts of water are added to 102 weight-parts of piperidine and 119 g of concentrated hydrochloric acid is added. Then 138 weight-parts of sodium-3-hydroxyacrylic acid ethyl ester are added to the solution at room temperature, stirred for 2 hours, and extracted with ethyl acetate. In the work-up by distillation, 123 weight-parts of 3-piperidinoacrylic acid ethyl ester are obtained, corresponding to a yield of 67.2% of the theory.

EXAMPLE 7

138 weight-parts of sodium-3-hydroxyacrylic acid ethyl ester are added to 87.6 weight-parts of n-butylamine, 177 weight-parts of water, and 117 weight-parts of concentrated hydrochloric acid; the mixture is stirred for 2 hours and extracted with diethyl ether. In the work-up by distillation, 104 weight-parts of 3-(n-butylamino)-acrylic acid ethyl ester are obtained, corresponding to a yield of 60.8% of the theory.

EXAMPLE 8

97 weight-parts of dimethylamine hydrochloride are dissolved in 250 weight-parts of water, and 200 weight-parts of sodium 3-hydroxy-2-phenyl acrylic acid methyl ester are added. The mixture is stirred for 2 hours, and the organic phase is separated and distilled. 148 weight-parts of 3-dimethylamino-2-phenyl acrylic acid methyl ester are obtained, corresponding to a yield of 72.2% of the theory.

It will be understood that the specification and examples are illustrative but not limitative of the present invention and that other embodiments within the spirit and scope of the invention will suggest themselves to those skilled in the art.

We claim:

1. A method for the preparation of a 3-aminoacrylic acid esters of the general formula

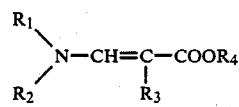

in which $R_1$ and $R_2$ represent H or identical or different straight-chain or branched alkyl moieties having 1 to 8 carbon atoms, or alkenyl moieties having 2 to 8 carbon atoms; $R_3$ represents hydrogen, straight-chain or branched alkyl moieties having 1 to 8 carbon atoms, or an isocyclic or aromatic ring, or in which $R_1$ and $R_2$ in common represents a component or piperidine and $R_4$ represents straight-chain or branched alkyl moieties having 1 to 8 carbon atoms, or an isocyclic or aromatic ring, comprising reacting an alkali salt of a beta-hydroxyacrylic acid ester of the general formula

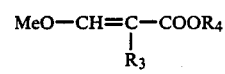

wherein $R_3$ and $R_4$ have the above meaning and Me is an alkali metal, with an amine salt of the general formula III

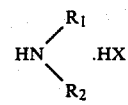

in which $R_1$ and $R_2$ have the above meaning and X is an anion of an inorganic or organic acid, by adding said ester of formula II as a solid, or in suspension in an acetic alkyl ester to an aqueous solution of said amine salt and allowing the reaction to proceed.

2. The method of claim 1, wherein the reaction is performed by the addition of a suspension formed in the production of alkali hydroxyacrylic acid ester in acetic acid alkyl ester.

3. The method of claim 1, wherein the amine salt is used in an excess of 0.05 to 1.5 moles.

4. The method of claim 1, wherein the alkali hydroxyacrylic acid ester is sodium-3-hydroxyethyl acrylate.

5. The method of claim 1, wherein the amine is a dialkyl amine.

6. The method of claim 3, wherein the amine salt is used in an excess of 0.05 to 1.5.

7. The method of claim 1, wherein the reaction occurs at a temperature in the range of 20° to 50° C.

8. The method of claim 7, wherein the reaction takes place at a temperature in the range of 20° to 30° C.

9. The method of claim 1, wherein the amine salt is dimethylamine hydrochloride.

10. The method of claim 1, wherein the aqueous solution contains an amount of water such that after the reaction has ended the alkali chloride content of a resulting solution is in the range of 20 to 25% before separation of the 3-aminoacrylic acid ester from the resulting solution.

11. The method of claim 1, wherein the amine is piperidine.

* * * * *